(12) United States Patent
Cocker et al.

(10) Patent No.: US 7,300,423 B2
(45) Date of Patent: Nov. 27, 2007

(54) SAFETY DEVICE WITH TRIGGER MECHANISM

(75) Inventors: Robin Craig Cocker, Cambridgeshire (GB); Anthony Jonathan Bedford, Cambridgeshire (GB); David Robert Gale, Harston Mill (GB)

(73) Assignee: Tyco Healthcare Group LP, Mansfield, MA (US)

( * ) Notice: Subject to any disclaimer, the term of this patent is extended or adjusted under 35 U.S.C. 154(b) by 301 days.

(21) Appl. No.: 10/716,771

(22) Filed: Nov. 19, 2003

(65) Prior Publication Data

US 2004/0162532 A1 Aug. 19, 2004

(30) Foreign Application Priority Data

Feb. 14, 2003 (GB) .................................. 0303437.8

(51) Int. Cl.
*A61M 5/00* (2006.01)
*A61M 5/32* (2006.01)

(52) U.S. Cl. .................... 604/263; 604/192; 604/162

(58) Field of Classification Search ................ 604/110, 604/263, 158, 162, 192, 197–199, 164.08, 604/164.07, 177, 165.03, 195, 168.01; 128/919; 600/573, 576
See application file for complete search history.

(56) References Cited

U.S. PATENT DOCUMENTS

| | | | |
|---|---|---|---|
| 1,779,451 A | 10/1930 | Sponsel | |
| 2,559,474 A | 7/1951 | Son | 128/215 |
| 2,700,385 A | 1/1955 | Ortiz | 128/215 |
| 2,836,942 A | 6/1958 | Miskel | 53/25 |
| 2,854,976 A | 10/1958 | Heydrich | 128/221 |
| 2,925,083 A | 2/1960 | Craig | |
| 2,953,243 A | 9/1960 | Roehr | 206/43 |
| 3,021,942 A | 2/1962 | Hamilton | 206/43 |
| 3,073,307 A | 1/1963 | Stevens | 128/221 |
| 3,074,542 A | 1/1963 | Myerson et al. | 206/43 |
| 3,134,380 A | 5/1964 | Armao | |
| 3,255,873 A | 6/1966 | Speelman | 206/56 |
| 3,294,231 A | 12/1966 | Vanderbeck | 206/63 |
| 3,323,523 A | 6/1967 | Scislowicz et al. | 128/214 |
| 3,329,146 A | 7/1967 | Waldman, Jr. | 128/221 |
| 3,333,682 A | 8/1967 | Burke | 206/43 |
| 3,367,488 A | 2/1968 | Hamilton | 206/63 |
| 3,485,239 A | 12/1969 | Vanderbeck | 128/218 |
| 3,537,452 A | 11/1970 | Wilks | 128/214 |
| 3,587,575 A | 6/1971 | Lichtenstein | 128/215 |
| 3,610,240 A | 10/1971 | Harautuneian | 128/214 |
| 3,645,835 A | 2/1972 | Hodgson | 161/146 |
| 3,658,061 A | 4/1972 | Hall | 128/214 |

(Continued)

FOREIGN PATENT DOCUMENTS

DE 19518803 12/1995

(Continued)

*Primary Examiner*—Matthew F. DeSanto (57) ABSTRACT

A safety device, usable in particular with hypodermic needles, and incorporating a trigger mechanism which when activated primes the device to initiate the unsheathing of the needle in use by flexing one or more needle-surrounding legs away from the needle axis; the initial priming and leg-flexing movement being caused by the interaction of an operative portion of the trigger with the or each said leg or with a member connected operatively thereto; characterised by the feature that, when such movement occurs, the trigger end interacts with the leg or the said, part connected thereto in a manner which positively latches and retains the two in engagement.

28 Claims, 7 Drawing Sheets

U.S. PATENT DOCUMENTS

| | | | |
|---|---|---|---|
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,918,446 A | 11/1975 | Buttaravoli | 128/133 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,725,267 A | 2/1988 | Vaillancourt | |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 604/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | |
| 4,863,435 A | 9/1989 | Sturman et al. | |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,921,490 A | 5/1990 | Spier et al. | |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A * | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A * | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 4,998,922 A | 3/1991 | Kuracina et al. | |
| 5,000,744 A | 3/1991 | Hoffman et al. | 604/232 |
| 5,015,240 A | 5/1991 | Soproni et al. | 604/192 |
| 5,015,242 A | 5/1991 | Heifetz | |
| 5,057,089 A | 10/1991 | Greco | 604/198 |
| 5,059,180 A | 10/1991 | McLees | 604/110 |
| 5,059,184 A | 10/1991 | Dyke | |
| 5,069,669 A | 12/1991 | Kole | |
| 5,092,851 A | 3/1992 | Ragner | |
| 5,108,379 A | 4/1992 | Dolgin et al. | 604/198 |
| RE34,045 E | 8/1992 | McFarland | 604/198 |
| 5,135,509 A | 8/1992 | Olliffe | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A * | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,295,972 A | 3/1994 | Mischenko | |
| 5,295,983 A | 3/1994 | Kubo | |
| 5,304,137 A | 4/1994 | Fluke | |
| 5,312,368 A | 5/1994 | Haynes | 604/192 |
| 5,312,369 A | 5/1994 | Arcusin et al. | 604/192 |
| 5,334,158 A | 8/1994 | McLees | 604/110 |
| 5,348,544 A | 9/1994 | Sweeney et al. | 604/192 |
| 5,356,387 A | 10/1994 | Sirbola | |
| 5,356,392 A | 10/1994 | Firth et al. | 604/198 |
| 5,372,589 A | 12/1994 | Davis | 604/180 |
| 5,374,255 A | 12/1994 | Nathan et al. | |
| 5,403,283 A | 4/1995 | Luther | 604/164 |
| 5,403,286 A | 4/1995 | Lockwood, Jr. | 604/110 |

| | | | |
|---|---|---|---|
| 5,407,436 A | 4/1995 | Toft et al. .................... 604/195 |
| 5,411,492 A | 5/1995 | Sturman et al. ............ 604/263 |
| 5,423,765 A | 6/1995 | Hollister .................... 604/192 |
| 5,423,766 A | 6/1995 | Di Cesare ................... 604/192 |
| 5,425,720 A | 6/1995 | Rogalsky et al. ........... 604/198 |
| 5,445,618 A | 8/1995 | Adobbati .................... 604/192 |
| 5,447,501 A | 9/1995 | Karlsson et al. ............ 604/198 |
| 5,466,223 A | 11/1995 | Bressler et al. |
| 5,480,385 A | 1/1996 | Thorne et al. .............. 604/110 |
| 5,486,164 A | 1/1996 | Streck |
| 5,487,733 A | 1/1996 | Caizza et al. ............... 604/110 |
| 5,487,734 A | 1/1996 | Thorne et al. .............. 604/195 |
| 5,490,841 A | 2/1996 | Landis ....................... 604/110 |
| 5,498,243 A | 3/1996 | Vallelunga et al. ......... 604/197 |
| 5,531,694 A | 7/1996 | Clemens et al. ............ 604/110 |
| 5,533,980 A | 7/1996 | Sweeney et al. ............ 604/192 |
| 5,536,240 A | 7/1996 | Edwards et al. .............. 604/22 |
| 5,538,508 A | 7/1996 | Steyn ......................... 604/192 |
| 5,542,927 A | 8/1996 | Thorne et al. .............. 604/110 |
| 5,549,568 A | 8/1996 | Shields ....................... 604/192 |
| 5,549,570 A | 8/1996 | Rogalsky .................... 604/198 |
| 5,549,708 A | 8/1996 | Thorne et al. .............. 604/110 |
| 5,562,629 A | 10/1996 | Haughton et al. .......... 604/198 |
| 5,562,631 A | 10/1996 | Bogert ....................... 604/164 |
| 5,573,510 A | 11/1996 | Isaacson .................... 604/158 |
| 5,584,816 A | 12/1996 | Gyure et al. ................ 604/192 |
| 5,584,818 A | 12/1996 | Morrison .................... 604/197 |
| 5,599,318 A | 2/1997 | Sweeney et al. ............ 604/263 |
| 5,611,782 A | 3/1997 | Haedt ......................... 604/198 |
| 5,643,220 A | 7/1997 | Cosme ....................... 604/192 |
| 5,672,161 A | 9/1997 | Allen et al. ................. 604/263 |
| 5,695,474 A | 12/1997 | Daugherty .................. 604/162 |
| 5,695,477 A | 12/1997 | Sfikas ........................ 604/241 |
| 5,700,249 A | 12/1997 | Jenkins ....................... 604/263 |
| 5,735,827 A | 4/1998 | Adwers et al. ............. 604/263 |
| 5,738,665 A | 4/1998 | Caizza et al. ............... 604/263 |
| 5,746,718 A | 5/1998 | Steyn ......................... 604/192 |
| 5,746,726 A | 5/1998 | Sweeney et al. ............ 604/263 |
| 5,755,699 A | 5/1998 | Blecher et al. ............. 604/198 |
| 5,814,018 A | 9/1998 | Elson et al. ................. 604/110 |
| 5,817,064 A | 10/1998 | DeMarco et al. ........... 604/198 |
| 5,823,997 A | 10/1998 | Thorne ....................... 604/110 |
| 5,843,041 A | 12/1998 | Hake et al. ................. 604/198 |
| 5,879,330 A | 3/1999 | Bell ............................. 604/93 |
| 5,891,092 A | 4/1999 | Castellano |
| 5,910,130 A | 6/1999 | Caizza et al. ............... 604/110 |
| 5,910,132 A | 6/1999 | Schultz |
| 5,919,168 A | 7/1999 | Wheeler ..................... 604/198 |
| 5,921,969 A | 7/1999 | Vallelunga et al. ......... 604/263 |
| 5,925,020 A | 7/1999 | Nestell ....................... 604/198 |
| 5,951,522 A | 9/1999 | Rosato et al. ............... 604/177 |
| 5,951,525 A | 9/1999 | Thorne et al. .............. 604/198 |
| 5,957,892 A | 9/1999 | Thorne ....................... 604/162 |
| 5,976,111 A | 11/1999 | Hart |
| 5,980,488 A | 11/1999 | Thorne ....................... 604/110 |
| 5,997,504 A | 12/1999 | Bell ............................. 604/93 |
| 6,015,397 A | 1/2000 | Elson et al. ................. 604/192 |
| 6,036,675 A | 3/2000 | Thorne et al. .............. 604/232 |
| 6,149,629 A | 11/2000 | Wilson et al. .............. 604/198 |
| 6,171,284 B1 | 1/2001 | Kao et al. ................... 604/192 |
| RE37,110 E | 3/2001 | Hollister .................... 206/365 |
| 6,224,576 B1 | 5/2001 | Thorne et al. .............. 604/198 |
| RE37,252 E | 7/2001 | Hollister .................... 206/364 |
| 6,254,575 B1 | 7/2001 | Thorne, Jr. et al. ......... 604/198 |
| 6,280,420 B1 | 8/2001 | Ferguson et al. ........... 604/198 |
| 6,334,857 B1 | 1/2002 | Hollister et al. ............ 604/263 |
| 6,582,397 B2 | 6/2003 | Alesi et al. ................. 604/110 |
| 6,592,556 B1 | 7/2003 | Thorne ....................... 604/192 |
| 6,635,032 B2 | 10/2003 | Ward, Jr. .................... 604/192 |
| 6,719,731 B2* | 4/2004 | Parmigiani ................. 604/192 |
| 2001/0039401 A1 | 11/2001 | Ferguson et al. |
| 2002/0004650 A1 | 1/2002 | Kuracina et al. |
| 2002/0072716 A1 | 6/2002 | Barrus et al. |
| 2003/0004465 A1 | 1/2003 | Ferguson et al. |
| 2003/0181870 A1* | 9/2003 | Bressler et al. ............. 604/263 |
| 2003/0181871 A1* | 9/2003 | Wilkinson et al. .......... 604/263 |

FOREIGN PATENT DOCUMENTS

| | | |
|---|---|---|
| EP | 0 144 483 | 6/1985 |
| EP | 0 344 606 A2 | 12/1989 |
| EP | 0 457 477 B1 | 11/1991 |
| EP | 0 485 345 B1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 A2 | 1/1998 |
| EP | 0 815 890 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| GB | 1233302 | 5/1971 |
| GB | 2 283 429 A | 5/1995 |
| GB | 2 369 779 | 12/2002 |
| JP | 10-76007 | 3/1998 |
| JP | 10-127765 | 5/1998 |
| NL | 9000909 | 4/1990 |
| NL | 9001664 | 7/1990 |
| WO | WO87/07162 | 12/1987 |
| WO | WO 89/04681 | 6/1989 |
| WO | WO89/07955 | 9/1989 |
| WO | WO93/02728 | 2/1993 |
| WO | WO93/17732 | 9/1993 |
| WO | WO94/01152 | 1/1994 |
| WO | WO94/19036 | 9/1994 |
| WO | WO97/31666 | 4/1997 |
| WO | WO98/07463 | 2/1998 |
| WO | WO98/10816 | 3/1998 |
| WO | WO98/11928 | 3/1998 |
| WO | WO98/13081 | 4/1998 |
| WO | WO 00/16832 | 3/2000 |
| WO | WO 00/38765 | 6/2000 |
| WO | WO 01/32241 A1 | 5/2001 |
| WO | WO 01/32244 A1 | 5/2001 |

* cited by examiner

FIG. 5D

SAFETY DEVICE WITH TRIGGER MECHANISM

FIELD OF THE INVENTION

The invention relates to a safety device, and in particular a trigger mechanism thereof, for hypodermic needles.

BACKGROUND TO THE INVENTION

This invention takes as its starting point PCT application number PCT/GB00/04416 (SCIENTIFIC GENERICS LIMITED) filed 20 Nov. 2000 and entitled 'Safety Device'. The closest prior art known to the applicant is this PCT application and any art acknowledged or on record for its patent prosecution since filing.

FIGS. 5a–5g in PCT application number PCT/GB00/04416 and their associated text explain that formed on top of each arm, 541, 542 towards the back inside edge of each, is a first (540b) and a second (540a) half of a priming button 540, which, when pushed forwards by a user, causes the back halves 541a, 542a of the locking arms to pivot outwardly about the hinge regions 541d, 542d.

This PCT-published priming button arrangement 540 etc has been superseded by the present invention which not only works much better but on quite different principles. These differences, and their inherently inventive nature when compared with this most relevant prior art document, will become apparent as this present specification unfolds.

Other trigger mechanisms exist in this field and can be broadly summarised as:
  Those using single sided spring actions to return to the safe position, these have a tendency for the end caps to tilt towards the needle axis in use and have the potential to snag the needle tip preventing use;
  Those using coiled/compressed spring actions to return to the safe position; here the number of parts in the assembly precludes the use of modem single-piece moulding techniques, incurring undesirable additional manufacturing costs.

An objective of the present invention is to provide an improved safety device incorporating a trigger mechanism that includes a priming function which guards against accidental so-called "needle stick" when not in use and enables the needle to be unsheathed during use in a controlled manner and then automatically resheathed to ensure safe further contact.

SUMMARY OF THE INVENTION

In its broadest aspect the invention provides a safety device with trigger mechanism which is intended to form part of, and to operate in conjunction with, a needle-sheathing safety device of the general kind exemplified by the FIGS. 5a–5g embodiments of PCT/GB00/04416 but whose scope is defined by the claims of this present specification.

Those claims, as numbered and set out at the end of this disclosure, form an inherent part of the disclosure in their own right.

BRIEF DESCRIPTION OF THE DRAWINGS

The accompanying drawings show, by way of example only, one safety device trigger mechanism embodying the invention.

In the drawings (in which FIGS. 1a to 1g correspond to FIGS. 5a to 5g of PCT/GB00/04416):

FIG. 1b is a schematic cross-sectional view of the prior art safety device of FIG. 1a along the line b—b in the safe position of FIG. 1a;

FIGS. 1a to 1g should first be studied in conjunction with the relevant text of application PCT/GB00/04416. The present description proceeds from there.

DETAILED DESCRIPTION OF THE EMBODIMENT

With reference to FIGS. 2 to 5 a safety device assembly 10 is presented comprising a needle receiving portion 11, a sheath portion 12 and a trigger mechanism 13.

The needle-receiving portion 11 operably receives and holds a needle "N"(see FIGS. 4a, 4b, 4c) and/or needle luer combination and assembly of such.

The sheath portion 12 comprises a nose plate 14 having a bore 15 therethrough, with resiliently flexible legs 16, 17 extending between the needle receiving portion 11 and the nose plate 14 and operably connected at these junctures by hinges 18, 19 on both legs 16, 17.

The safety device assembly 10 is formed by a one piece injection moulding process.

Each resiliently flexible leg 16, 17 of the safety device 10 has a central knee joint 20, 21 separating the back portion of the legs 16a, 17a and the front portion of the legs 16b, 17b. The configuration of the leg portions 16a, 17a; and knee joints 20, 21 ensure that longitudinal forces acting on the nose plate 14 reinforce the natural bias. Resilient means in the form of an elastic band 22 disposed over the rear portion of the legs 16a, 17a prevents deforming and outward flexing of the legs 16, 17 increasing resistance to accidental needle stick when the assembly is unprimed and ensuring automatic return of arms 16, 17 and the nose plate 14 to the extended position when the assembly is no longer in the primed position. The band 22 is held in place by securing lugs 23a, 23b disposed on opposing legs 16a, 17a on the outside face of the legs 16a, 17a. Intermediate the securing lugs 23a, 23b about the upper face of the legs 16a, 17a is located release means 24 comprising rigid tabs 24a, 24b. The tabs 24a, 24b form a triangular cut-out region which acts as a lead-in for the trigger mechanism 13.

The trigger mechanism 13 comprises an elongate actuating lever 13 fixably attached at one end to the needle receiving portion 11 and having a second end disposed over the back region of the legs 16, 17 when forced between tabs 24a, 24b it separates the legs 16, 17 in a direction away from each other, overcoming the inherent bias of the legs 16, 17 and the restraining force of band 22.

The tab-engaging portion 25 of the lever 13 is shaped and sized to engage the release means 24 and separate the rigid tabs 24a, 24b when pressed in a downward direction and in turn separate the legs 16, 17 whilst not obstructing the passage of the needle N.

The profile of the elongate actuator lever 13 comprises a large radius 26 at the rear and a smaller radius 27 at the front. A strengthening rib 28 on the underside of the actuating lever 13 is disposed between the engaging portion 25 and the entirety of the small radius 27.

In operation, a user would grasp the safety device assembly 10 by placing a thumb on the upper face of the trigger lever 13 above the strengthening rib 28 whilst at the same time having a finger, on the underside of the assembly, supporting the assembly when the user then presses the trigger, the pressure of such a movement forces the engaging portion of the actuating lever 13 between the release means 24 and separates the tabs 24a, 24b, the engaging portion 25 is progressively securely latched between and under each leg 16a, 17a in a position immediately below the tabs 24a, 24b.

In this, the so-called primed position, subsequently applied longitudinal forces acting on the nose plate 14 will cause the legs 16, 17 to flex outwardly and unsheath the needle N for use. Performing the injection (i.e. continuing such longitudinal application of force along the needle axis) causes the legs 16, 17 to flex apart to a maximum position and the actuating lever 13 engaging portion 25 is then released from its secured latched position and rises up, under its own resilience, out of the way of the legs.

Figure 1A:
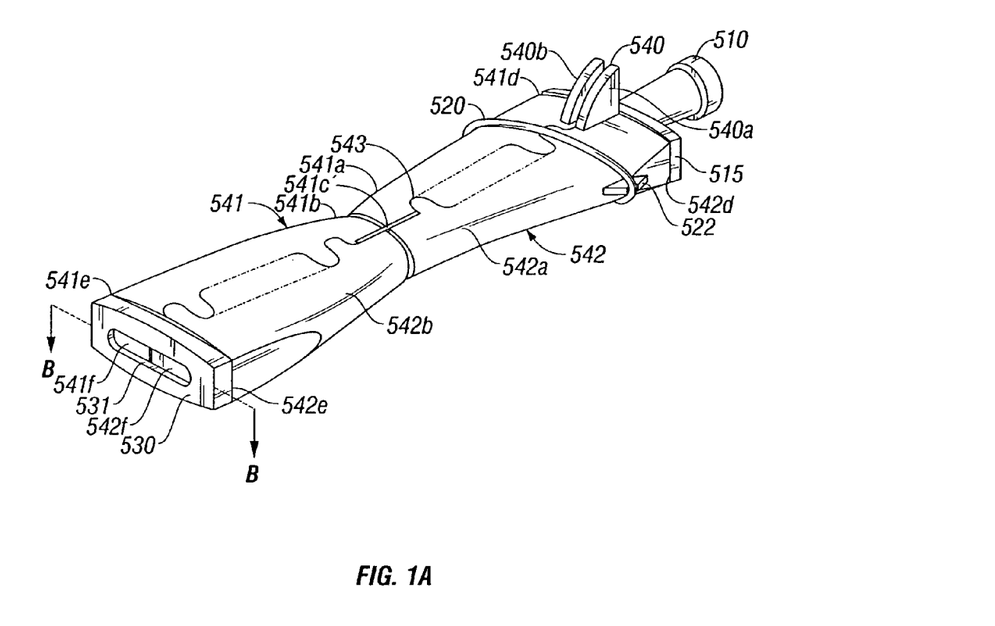
FIG. 1a is a perspective view of the closest prior art safety device in which pivoted locking arms extend along the length of the device.
Figure 1B:
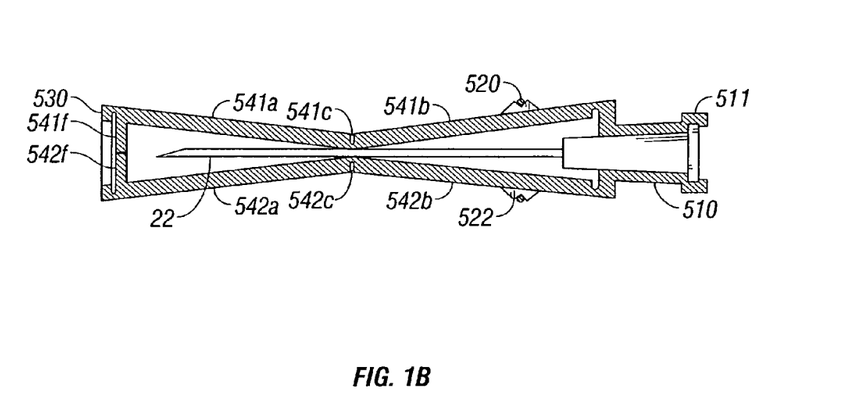
Figure 1C:
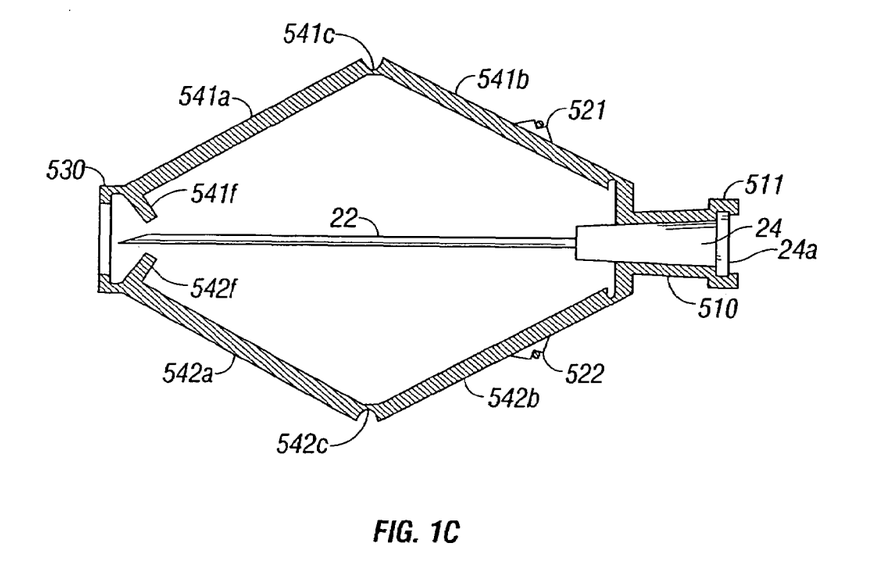
FIG. 1c is a schematic cross-sectional view of the prior art safety device of FIG. 1a along the line b—b in a primed position.
Figure 1D:
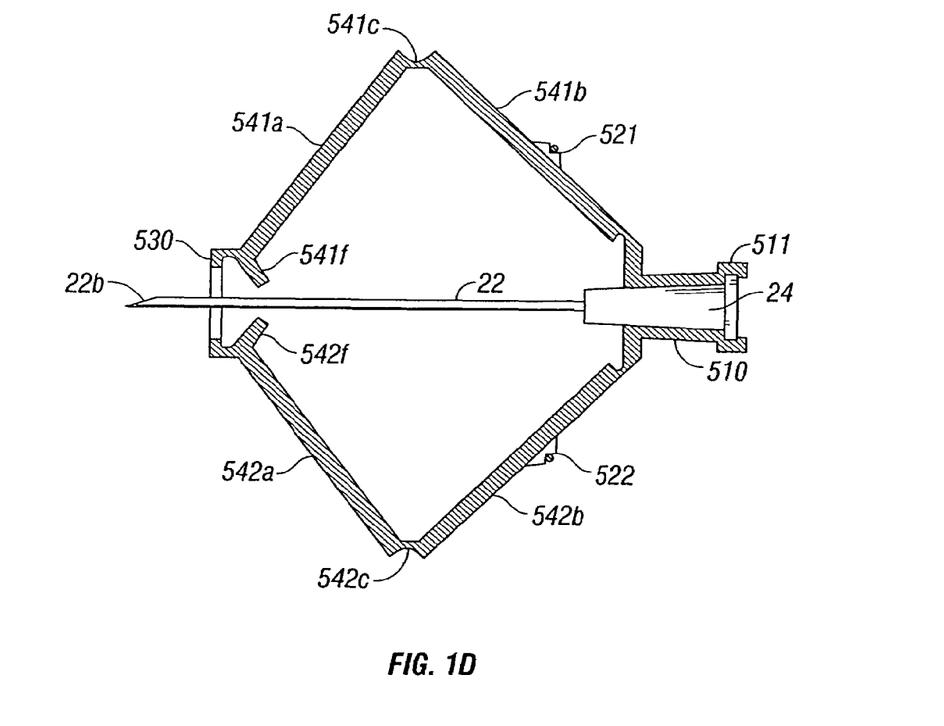
FIG. 1d is a schematic cross-sectional view of the prior art safety device of FIG. 1a along the line b—b in an injection position.
Figure 1E:
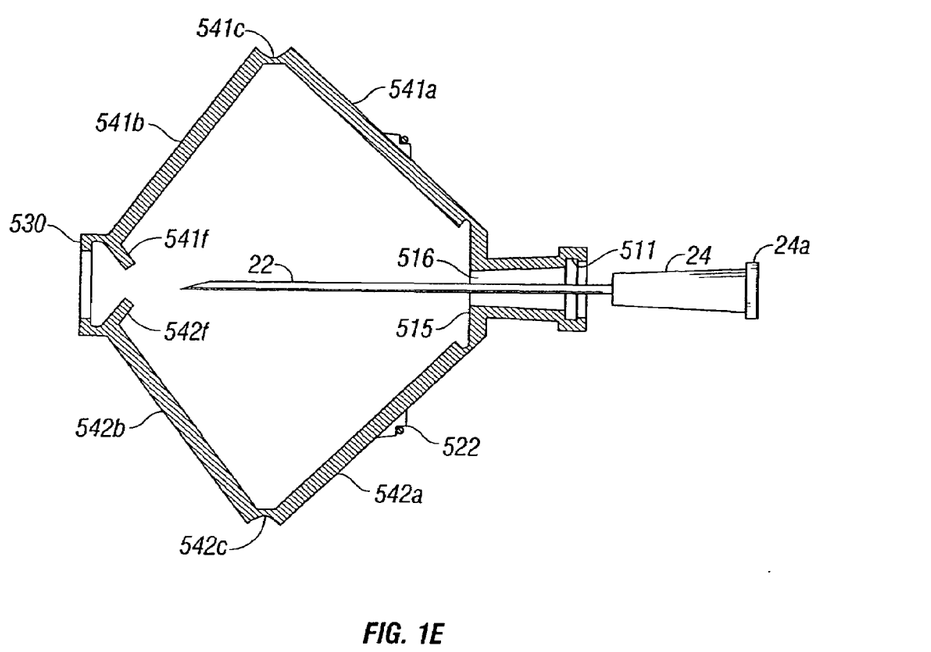
FIG. 1e is a schematic cross-sectional view similar to FIGS. 1b to 1c showing the prior art safety device and a needle and needle-luer combination, illustrating how the combination is mounted into the prior art safety device.
Figure 1F:
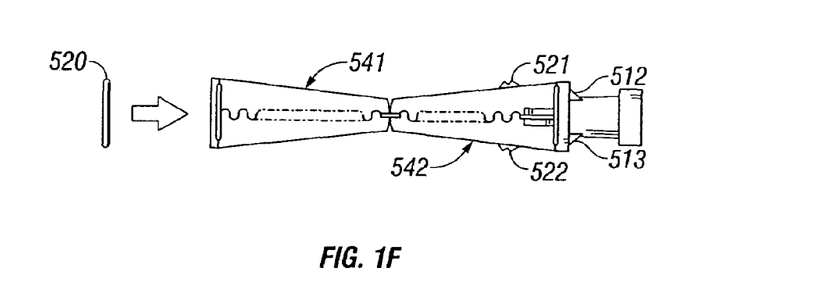
FIGS. 1f and 1g are schematic plan views of the prior art safety device of FIGS. 1a to 1e illustrating how an elastic band is mounted onto the prior art safety device.
Figure 1G:
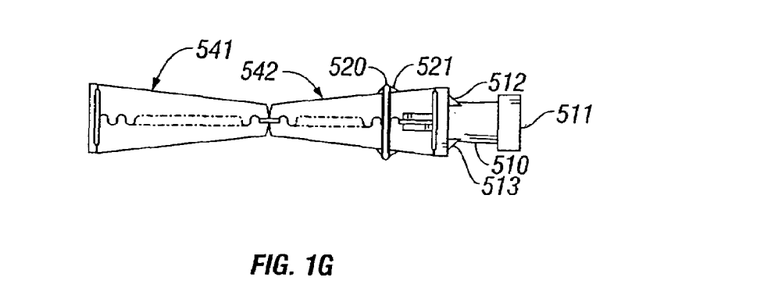
Figure 2:
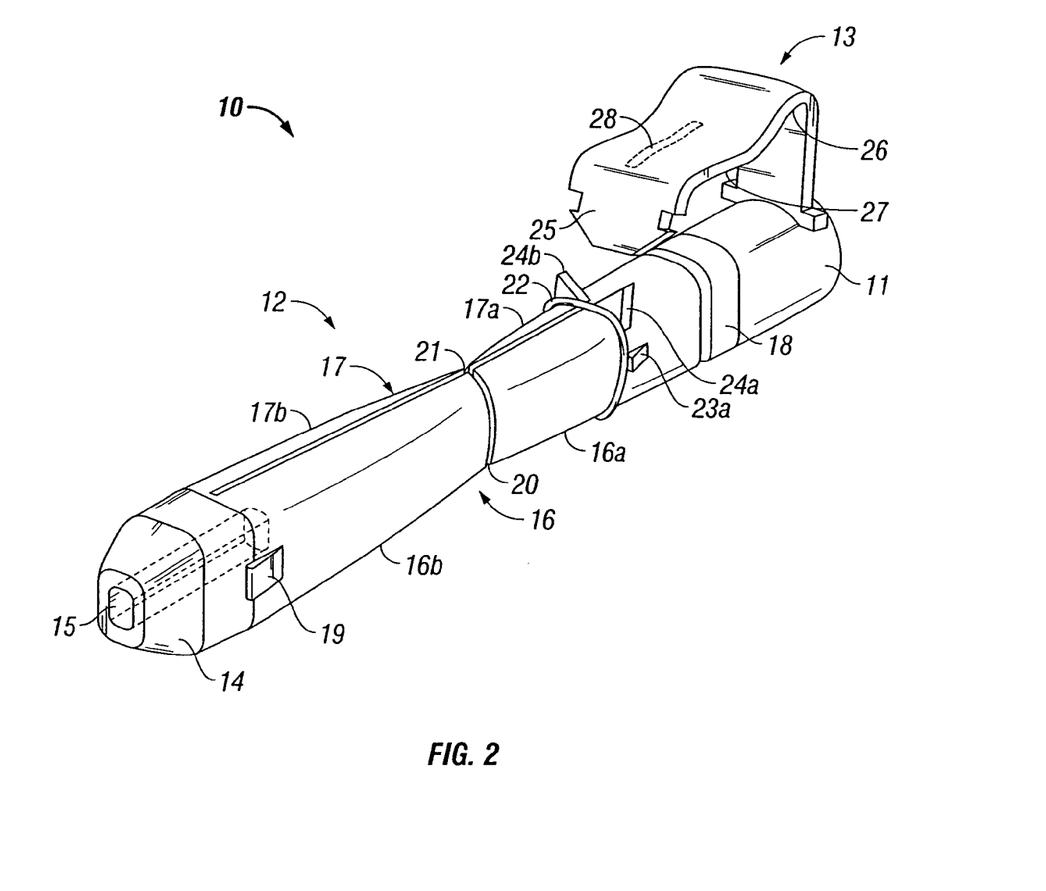
FIG. 2 is a perspective view of the safety device and trigger mechanism according to the invention in which the trigger mechanism is in the unprimed position.
Figure 3:
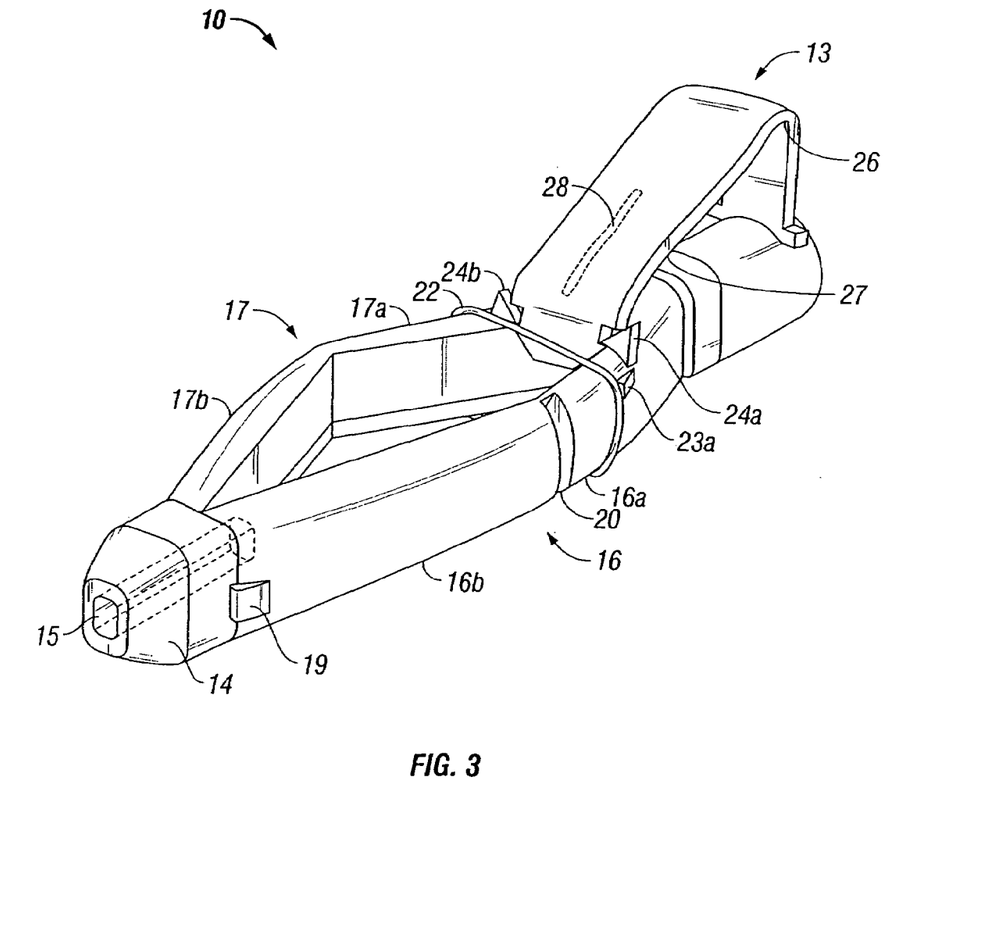
FIG. 3 is a perspective view showing that same trigger mechanism in the primed position.
Figure 4A:
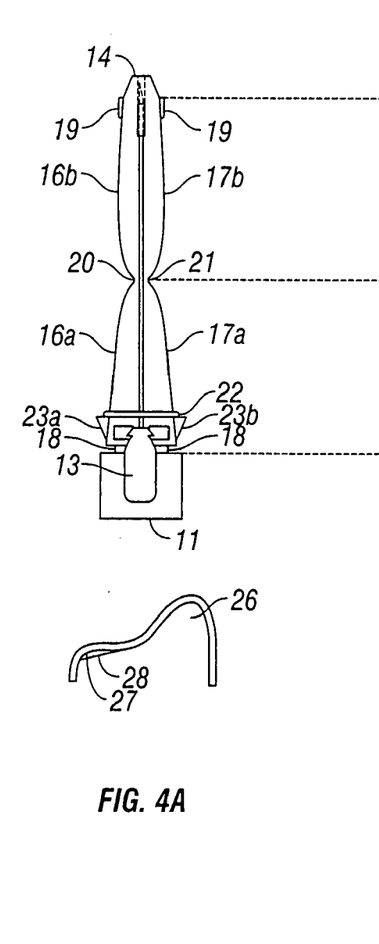
FIGS. 4a, 4b and 4c are schematic cross-sectional views illustrating the effect of the trigger mechanism on the geometry of the safety device in respectively the unprimed, primed and the automatic release from primed positions.
Figure 4B:
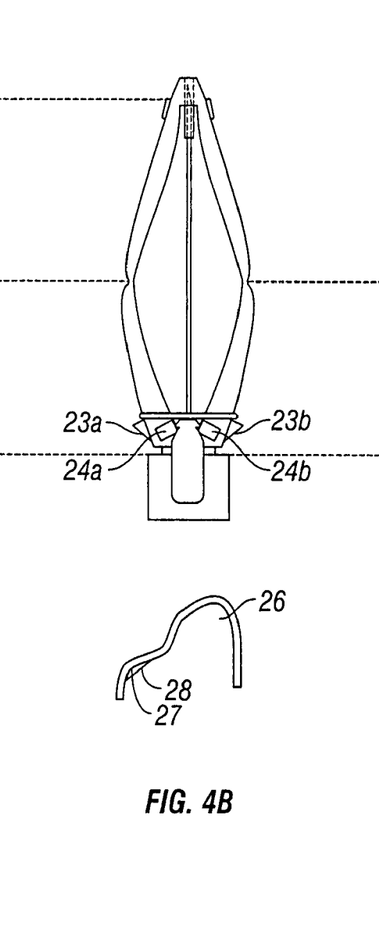
Figure 4C:
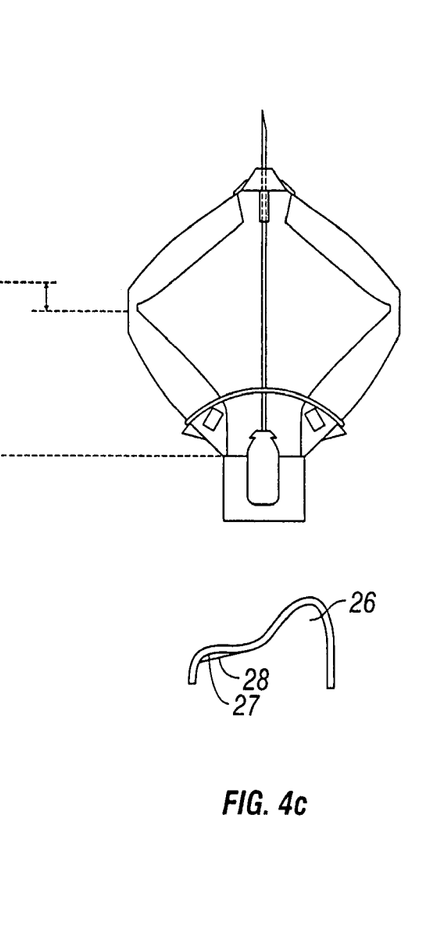
Figure 5A:
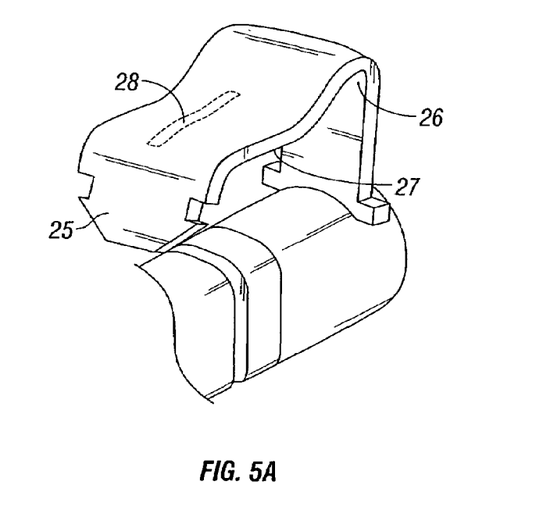
FIG. 5a is an enlarged perspective view of the trigger mechanism.
Figure 5B:
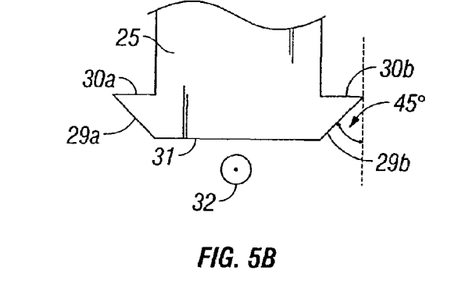
FIG. 5b is a preferred profile of the trigger mechanism.
Figure 5C:
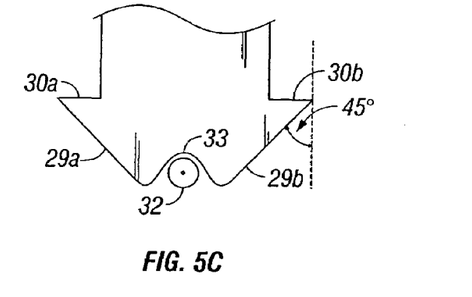
FIG. 5c is an alternative profile of the trigger mechanism.
Figure 5D:
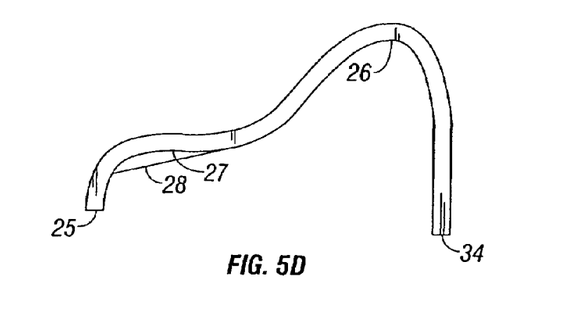
FIG. 5d is a schematic cross-sectional view of the trigger mechanism.

When the longitudinal force acting on the nose plate 14 is removed, the needle retracts; the natural resilience of the legs 16, 17 plus the action of band 22 causes the legs 16, 17 to automatically close around the needle N until they are once more in the closed position of FIG. 2. They are ten geometrically so biased that further longitudinal forces acting on the nose plate 14 will be resisted rather than cause the needle N to be exposed.

The double-curved profile of the trigger mechanism 13 gives it in-built equilibrium retaining the relative positions between the engaging portion above the release means 24. Its shape also intuitively leads the user to correctly use the assembly 10 to perform an injection. In other words, he will tend naturally to downwardly press it rather than attempt to push it forwards.

The trigger has a number of other advantageous features.

The downward engaging movement of portion 25 as it separates the legs 16, 17 is such that further downward pressure as the engaging portion 25 is latched into a primed position tends to retain inline the centres of the legs 20, 21 and the centre of the needle;

The end profile of the engaging portion 25 is so shaped to separate the arms 16, 17 evenly whilst retaining the geometry of the legs 16, 17—if the centres of the legs 20, 21 are not kept far enough apart one leg would have a tendency to lock and hinder movement but the present configuration ensure both legs 16, 17 move apart equally;

The end profile has a squared off front end, so that when the engaging portion 25 is latched in the primed position there is sufficient clearance for the needle N to move without impacting the trigger mechanism 13. In an alternative embodiment (FIG. 5c) it is so shaped and sized to embrace the needle N without restricting movement of the needle; this is also advantageous in its own right.

The curvy profile of the actuating lever 13 comprises two radii, a large rearward radius 26 to prevent the likelihood of plastic creep giving the assembly 10 a longer life, inherent-reusability and to assist the spring back action of the lever 13 and a smaller forward radius 27 giving the so-called working end of the lever 13 with the engaging portion 25 a low profile.

The strengthening rib 28 limits the deformation of the curved shape trigger 13, in use. It permits deformation in the first curve 26 which in turn assists spring-back but strengthens the second curve 27 restricting the movement of the engaging portion 25 downwards rather than forwards.

The invention claimed is:

1. A safety device comprising:
    a needle receiving portion;
    a sheath portion including first and second legs, the first and second legs having proximal ends supported by the needle receiving portion and distal ends spaced from the needle receiving portion, the first and second legs being movable from a first position in which the distal ends of the first and second legs are spaced from the needle receiving portion a first distance to a second position in which the distal ends of the first and second legs are spaced from the needle receiving portion a second distance, wherein the first distance is greater than the second distance; and
    a trigger supported adjacent to and movable independently of the proximal ends of the first and second legs, wherein the trigger is movable into sliding engagement with the first and second legs to move the first and second legs from the first position to the second position.

2. A safety device according to claim 1, further including a plate supported on a distal portion of the first and second legs, the plate defining a bore dimensioned to slidably receive a needle.

3. A safety device according to claim 1, wherein the first and second legs flex outwardly when the legs are moved from the first position to the second position.

4. A safety device according to claim 1, wherein the proximal ends of the first and second legs are hingedly connected to the needle receiving portion, the trigger being movable to a position between the first and second legs to urge the first and second legs apart and move the distal ends of the first and second legs from the first position to the second position.

5. A safety device according to claim 4, wherein the trigger includes a lever having first end attached to the needle receiving portion and a second end positioned adjacent the proximal ends of the first and second legs.

6. A safety device comprising:
a needle receiving portion
a sheath portion including first and second legs, the first and second legs having proximal ends supported by the needle receiving portion and distal ends spaced from the needle receiving portion, the first and second legs being movable from a first position in which the distal ends of the first and second legs are spaced from the needle receiving portion a first distance to a second position in which the distal ends of the first and second legs are spaced from the needle receiving portion a second distance, wherein the first distance is greater than the second distance; and
a trigger supported adjacent to the proximal ends of the first and second legs, wherein the trigger is movable into engagement with the first and second legs to move the first and second legs from the first position to the second position; and
a resilient member engaging the first and second legs to urge the first and second legs to their first position;
wherein the proximal ends of the first and second legs are hingedly connected to the needle receiving portion, the trigger being movable to a position between the first and second legs to urge the first and second legs apart and move the distal ends of the first and second legs from the first position to the second position.

7. A safety device according to claim 6, wherein the resilient member includes a resilient band.

8. A safety device according to claim 7, further including a pair of lugs positioned on the sheath to hold the resilient band in place.

9. A safety device according to claim 4, wherein each of the first and second legs includes a front portion and a rear portion interconnected by a bendable joint.

10. A safety device according to claim 1, further including at least one engagement surface positioned on the proximal end of the sheath portion, and wherein the trigger includes at least one engaging portion, the at least one engaging portion being movable into engagement with the at least one engagement surface of the sheath to retain the trigger in engagement with the first and second legs of the sheath.

11. A safety device according to claim 10, wherein the at least one engagement surface includes a pair of engagement surfaces.

12. A safety device according to claim 11, wherein each engagement surface of the pair of engagement surfaces includes an angled portion, the angled portions defining a lead-in to facilitate positioning of the trigger between the first and second legs.

13. A safety device according to claim 1, wherein the trigger has a double-curved profile.

14. A safety device according to claim 13, wherein the double-curved profile defines a first radius of curvature and a second radius of curvature, the first radius of curvature being smaller than the first radius of curvature.

15. A safety device according to claim 14, wherein the first radius of curvature is formed on the rear end of the trigger.

16. A safety device comprising:
a needle receiving portion;
a sheath portion extending distally from the needle receiving portion, the sheath portion including first and second legs; and
a trigger supported adjacent to and movable independently of a proximal end of the first and second legs; wherein the sheath portion is movable from an extended position in which the first and second legs shield a distal end of a needle positioned within the needle receiving portion to a primed position in response to movement of the trigger into sliding engagement with the first and second legs, wherein the sheath portion is configured such that in the extended position a longitudinal force acting on a distal end of the sheath portion maintains the sheath portion in the extended position and in the primed position a longitudinal force acting on the distal end of the sheath portion urges the sheath portion to a retracted position in which the distal end of the needle is exposed.

17. A safety device according to claim 16, wherein the first and second legs of the sheath portion are hingedly connected to the needle receiving portion.

18. A safety device according to claim 17, wherein each of the first and second legs includes a front portion and a rear portion interconnected by a joint.

19. A safety device according to claim 18, wherein the trigger is movable to a position between the first and second legs to urge the respective joints of the first and second legs apart and move the sheath portion to the primed position.

20. A safety device according to claim 19, wherein the trigger includes at least one engaging portion which is positioned to releasably engage an engagement surface of the sheath portion to retain the sheath portion in the primed position.

21. A safety device according to claim 20, wherein movement of the sheath portion from the primed position toward the retracted position disengages the at least one engaging portion of the trigger from the engagement surface of the sheath portion to facilitate movement of the sheath portion to the extended position.

22. A safety device comprising:
a needle receiving portion;
a sheath portion extending distally from the needle receiving portion, the sheath portion including first and second legs;
a trigger supported adjacent to and movable independently of a proximal end of the first and second legs; and a resilient member positioned to urge the sheath portion to the extended position.
wherein the sheath portion is movable from an extended position in which the first and second legs shield a distal end of a needle positioned within the needle receiving portion to a primed position in response to movement of the trigger into sliding engagement with the first and second legs, wherein the sheath portion is configured such that in the extended position a longitudinal force acting on a distal end of the sheath portion maintains the sheath portion in the extended position and in the primed position a longitudinal force acting on the distal end of the sheath portion urges the sheath portion to a retracted position in which the distal end of the needle is exposed.

23. A safety device according to claim 22, wherein the resilient member includes a resilient band.

24. A safety device according to claim 16, wherein the trigger includes a lever having a first end attached to the needle receiving portion and a second end positioned adjacent the proximal ends of the first and second legs.

25. A safety device comprising:
a needle receiving portion;
a needle extending from the needle receiving portion;
a sheath portion extending distally from the needle receiving portion, the sheath portion including first and second legs hingedly connected to the needle receiving portion, each of the first and second legs including a front portion and a rear portion interconnected by a joint;

a trigger supported adjacent to a proximal end of the first and second legs, the trigger being movable to a position between the first and second legs to urge the respective joints of the first and second legs apart and move the sheath portion to a primed position, the trigger having at least one engaging portion which is positioned to releasably engage an engagement surface of the sheath portion to retain the sheath portion in the primed position; and a resilient member positioned to urge the sheath portion to an extended position in which the first and second legs shield a distal end of the needle, wherein the sheath portion is movable from the extended position to the primed position in response to movement of the trigger into engagement with the first and second legs, the sheath portion being configured such that in the extended position a longitudinal force acting on a distal end of the sheath portion maintains the sheath portion in the extended position and in the primed position a longitudinal force acting on the distal end of the sheath portion urges the sheath portion to a retracted position in which the distal end of the needle is exposed, wherein movement of the sheath portion from the primed position to the retracted position disengages the at least one engaging portion of the trigger from the engagement surface of the sheath portion to facilitate movement of the sheath portion to the extended position.

26. A safety device according to claim 25, further including a plate supported on a distal portion of the first and second legs, the plate defining a bore dimensioned to slidably receive the needle.

27. A safety device according to claim 26, wherein the plate is a noseplate which covers the distal end of the needle in the extended position.

28. A safety device according to claim 25, wherein the first and second legs flex outwardly when the legs are moved from the extended position to the primed position.

* * * * *